United States Patent [19]
Krause

[11] Patent Number: 5,563,481
[45] Date of Patent: Oct. 8, 1996

[54] BRUSHLESS MOTOR

[75] Inventor: Kenneth W. Krause, Sandown, N.H.

[73] Assignee: Smith & Nephew Endoscopy, Inc., Andover, Mass.

[21] Appl. No.: 431,615

[22] Filed: May 1, 1995

Related U.S. Application Data

[63] Continuation of Ser. No. 135,297, Oct. 12, 1993, abandoned, which is a continuation-in-part of Ser. No. 867,871, Apr. 13, 1992, Pat. No. 5,270,622.

[51] Int. Cl.$^6$ ........................................ H02P 6/02
[52] U.S. Cl. ............................ 318/254; 318/138; 388/937
[58] Field of Search .................................... 318/138, 254, 318/439, 480, 569, 594, 600, 601; 388/937, 907.5

[56] References Cited

U.S. PATENT DOCUMENTS

| | | |
|---|---|---|
| 4,786,847 | 11/1988 | Daggett et al. . |
| 4,867,155 | 9/1989 | Isaacson . |
| 4,890,047 | 12/1989 | Maney . |
| 4,961,038 | 10/1990 | MacMinn . |
| 4,980,838 | 12/1990 | Daggett et al. . |
| 5,017,846 | 5/1991 | Young et al. . |
| 5,210,474 | 5/1993 | Oswald . |
| 5,317,243 | 5/1994 | Cameron . |

FOREIGN PATENT DOCUMENTS

| | | |
|---|---|---|
| 0148269 | 7/1985 | European Pat. Off. . |
| 2757132 | 12/1977 | Germany . |
| 2156172 | 3/1985 | United Kingdom . |

OTHER PUBLICATIONS

Patent Abstracts of Japan, vol. 10, No. 298 (P–505) 9 Oct. 1986 & JP–A–61 114 304 (Fujitsu Ltd) 2 Dec. 1986.
Patent Abstracts of Japan, vol. 13, No. 295 (E–783) 7 Jul. 1989 & JP–A–01 074 089 (Hitachi Ltd) 20 Mar. 1989.
Industry Applications Society IEEE–IAS–195 Annual Meeting, Nov. 1985, Toronto, Canada pp. 536–541, D. A. Topmiller et al., "A microprocessor . . . motor".
Electronic Engineering, vol. 58, No. 719, Nov. 1986, London GB, pp. 51–59; Phil Davies et al., "Three phase control and drive IC for brushless motors".
Machine Design, vol. 60, No. 13, 9 Jun. 1988, Cleveland US, pp. 140–144, XP000100657, Robert Benzer, "Single-chip brushless-motor controller".

*Primary Examiner*—Bentsu Ro
*Attorney, Agent, or Firm*—Fish & Richardson P.C.

[57] ABSTRACT

A wholly digital motor-control system for surgical instruments is disclosed. The signal processor and drive-controller communicate digitally through optical fibers. The system provides fail-safe shutdown in the event that communication ceases for longer than a predetermined time, torque limitation and control of complex movement patterns.

24 Claims, 11 Drawing Sheets

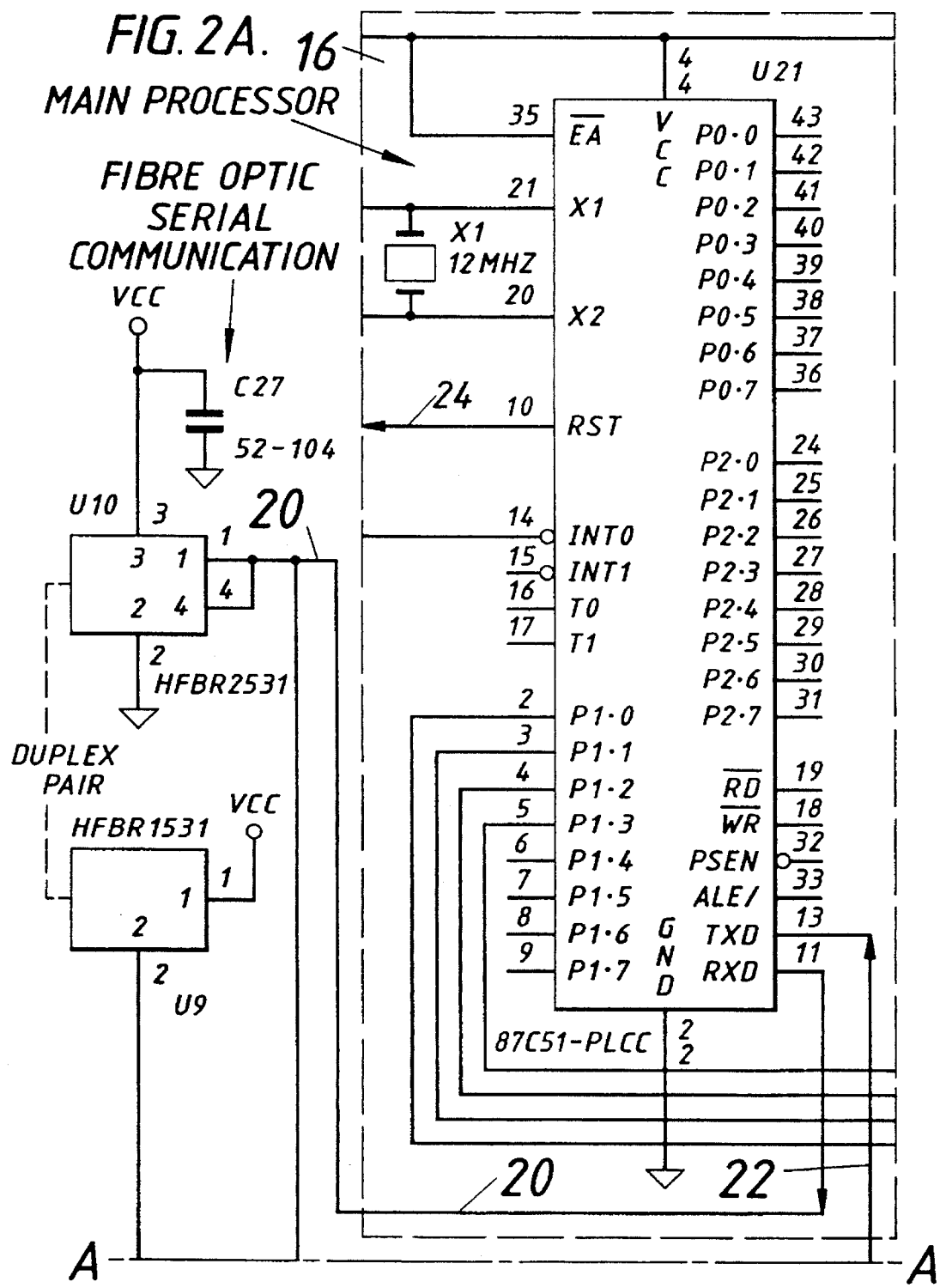

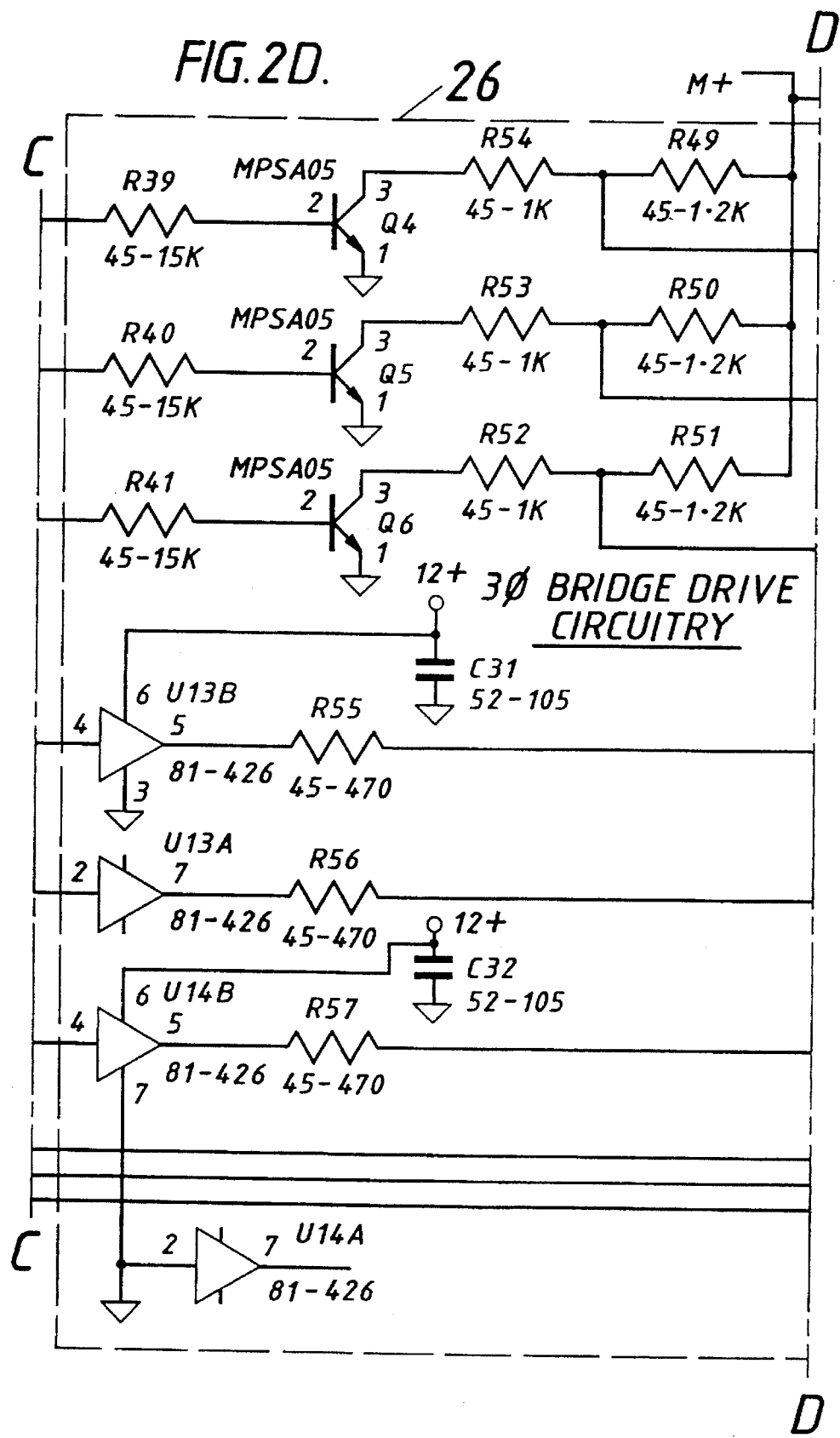

BRUSHLESS MOTOR

CROSS-REFERENCE

The present application is a continuation of application Ser. No. 08/135,297, filed Oct. 12, 1993, now abandoned, which is a continuation-in-part of application Ser. No. 07/867,871, filed Apr. 13, 1992, now U.S. Pat. No. 5,270,622.

BACKGROUND OF THE INVENTION

1. Field of the Invention

This invention generally relates to an all-digital motor control system and, more particularly, to a system for controlling the speed or armature position of a motor.

2. Description of Related Art

Speed control systems for controlling the speed of motors are generally known. However, such systems rely, at least in part, on analog signals and an analog-to-digital converter to convert the analog signals to digital signals for subsequent processing by digital signal processors. This adds hardware complexity and rigidity to the overall system. Also, the reliance on analog signals, at least in part, introduces an element of inaccuracy in motor speed control.

SUMMARY OF THE INVENTION

1. Objects of the Invention

It is a general object of this invention to advance the state of the art of control for motors.

It is another object of this invention to reduce the hardware requirement and system rigidity in such control systems.

Another object of this invention is to provide all-digital motor control systems, and with the attendant advantages of accuracy and speed of response.

Another object of the invention is to provide a motor control system which has particular application in surgical procedures.

Another is to provide a system which accurately controls surgical pumps, and motor driven surgical tools.

2. Features of the Invention

In keeping with these objects, and others which will become apparent hereinafter, one feature of this invention resides, briefly stated, in an all-digital control system for a motor having an armature. The system comprises a main digital signal processor for supplying a digital command signal indicative of a desired motor operation. A drive controller in direct digital communication with the main processor generates, for each phase, and in response to the command signal, a digital commutation signal to move the armature with a digital pulse width modulated signal having a duty cycle established by the input command signal.

The system further comprises switching means, e.g. a multi-phase bridge, in digital communication with the controller. The bridge is operative for generating, for each phase, and in response to each commutation signal and each pulse width modulated signal, a digital two-state control signal having an on-state which lasts for the duty cycle.

The system still further comprises means in digital communication with the controller, for generating, for each phase a digital tachometer signal indicative of armature position. The controller is further operative for processing the tachometer signal to generate a digital output signal indicative of the actual armature speed or position. The controller directly digitally communicates the output signal to the main processor.

In a preferred embodiment, the main processor and the drive controller are interconnected by, and digitally communicate through, a plurality of optical fibers. No analog signals and, or course, no analog-to-digital converters, are used anywhere in the speed control systems, thereby simplifying the hardware requirement for such system, and also eliminating any inaccuracies due to the presence of analog signals.

Another feature of this invention resides in shutting down the system upon the elapse of a predetermined time during which no input signal is received by the controller.

The control system has particular applications for surgical equipment, e.g. for accurately controlling pumps used to maintain pressure of saline solution inside a body cavity during an operation, and for motor driven surgical drills, saws, rasps, scalpels, scissors; and for limiting torque on the motor driven surgical instruments to avoid breakage and shattering of the instruments especially when inside a patient.

The novel features which are considered as characteristic of the invention are set forth in particular in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWINGS

FIGS. 2A–2E are a detailed electrical schematic of the system of FIG. 1;

DETAILED DESCRIPTION OF THE PREFERRED EMBODIMENT

Figure 1:
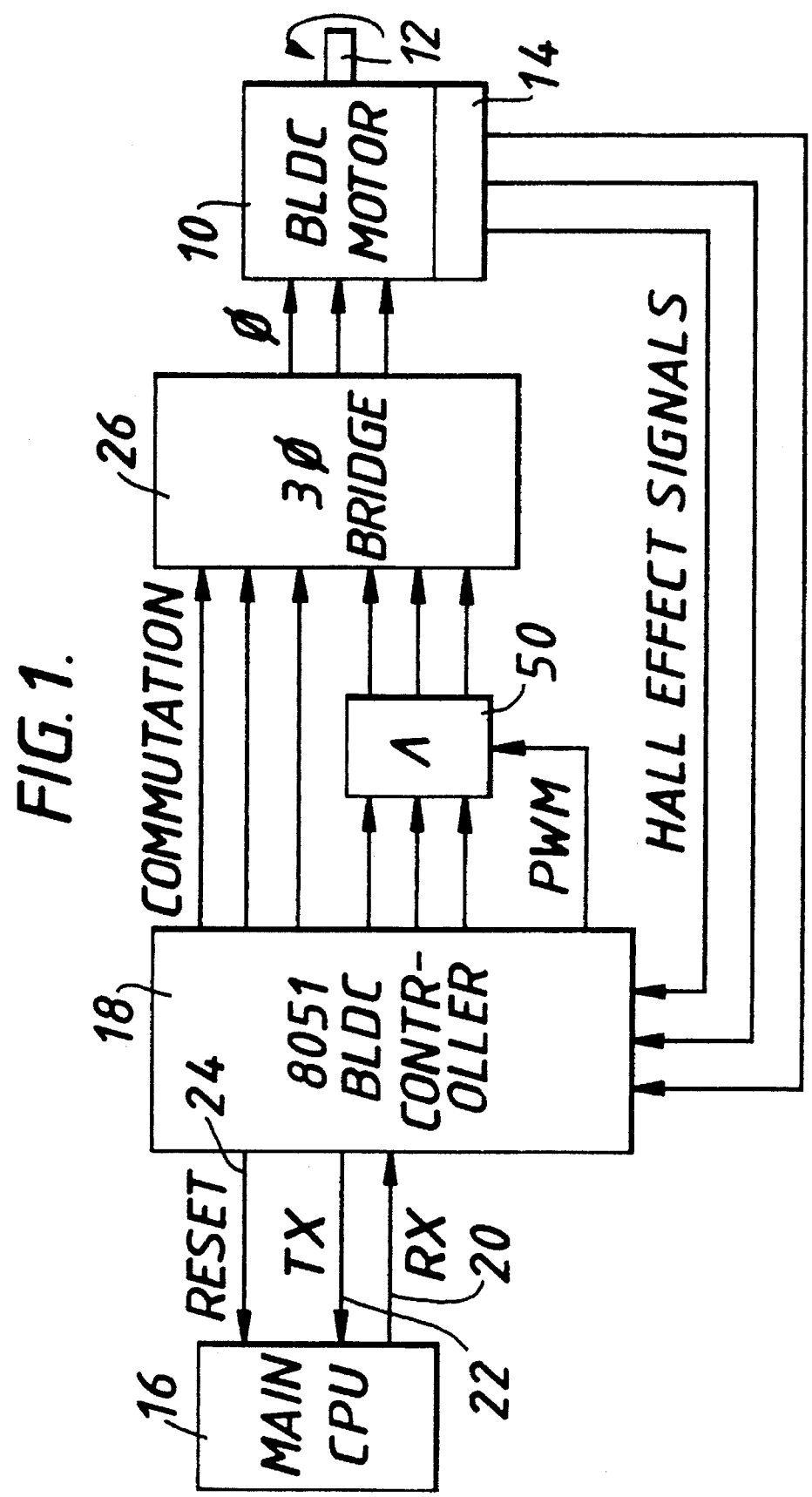
FIG. 1 is a general block diagram of the overall all-digital speed control system according to this invention.
Figure 2B:
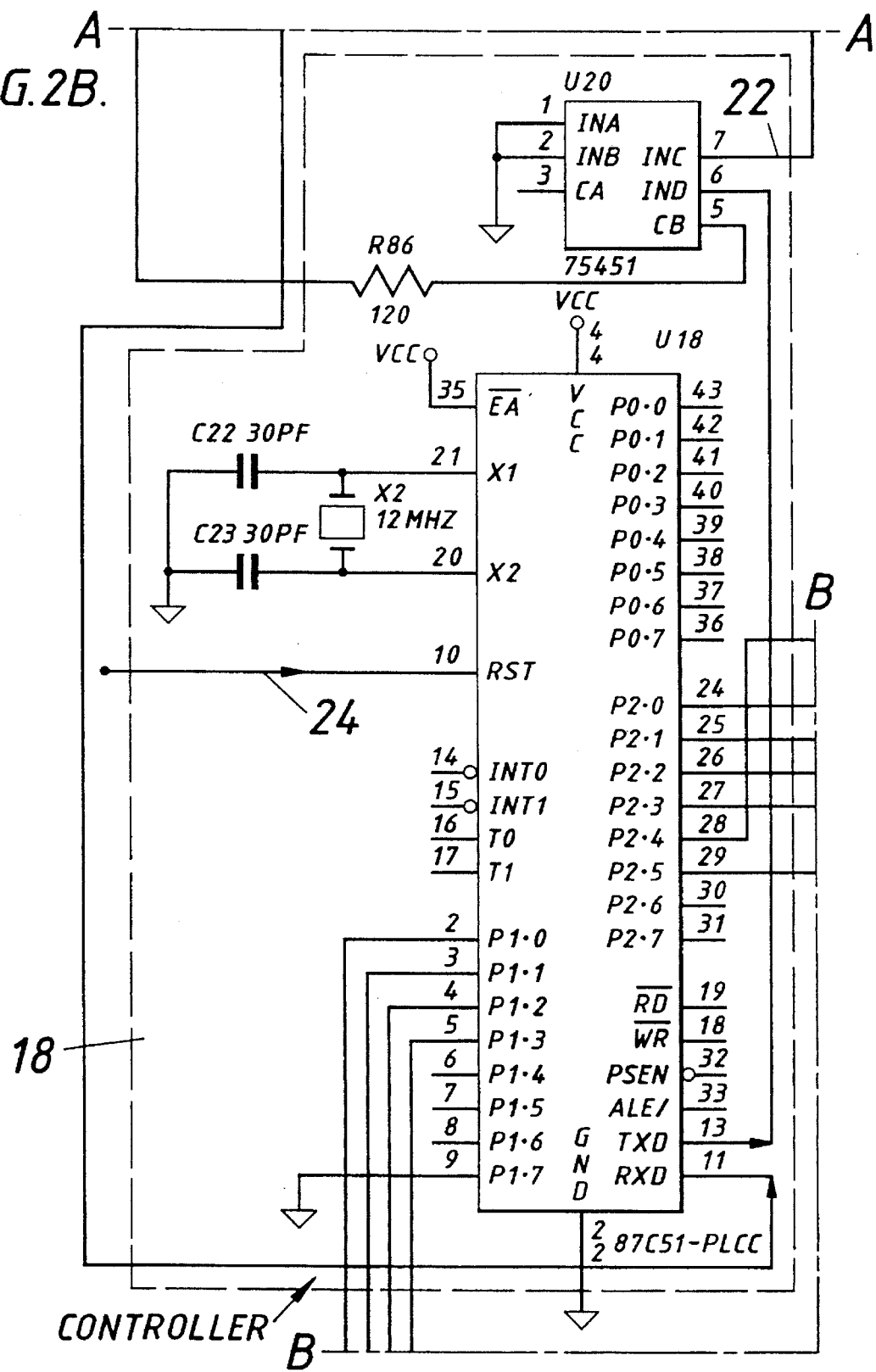
Figure 2C:
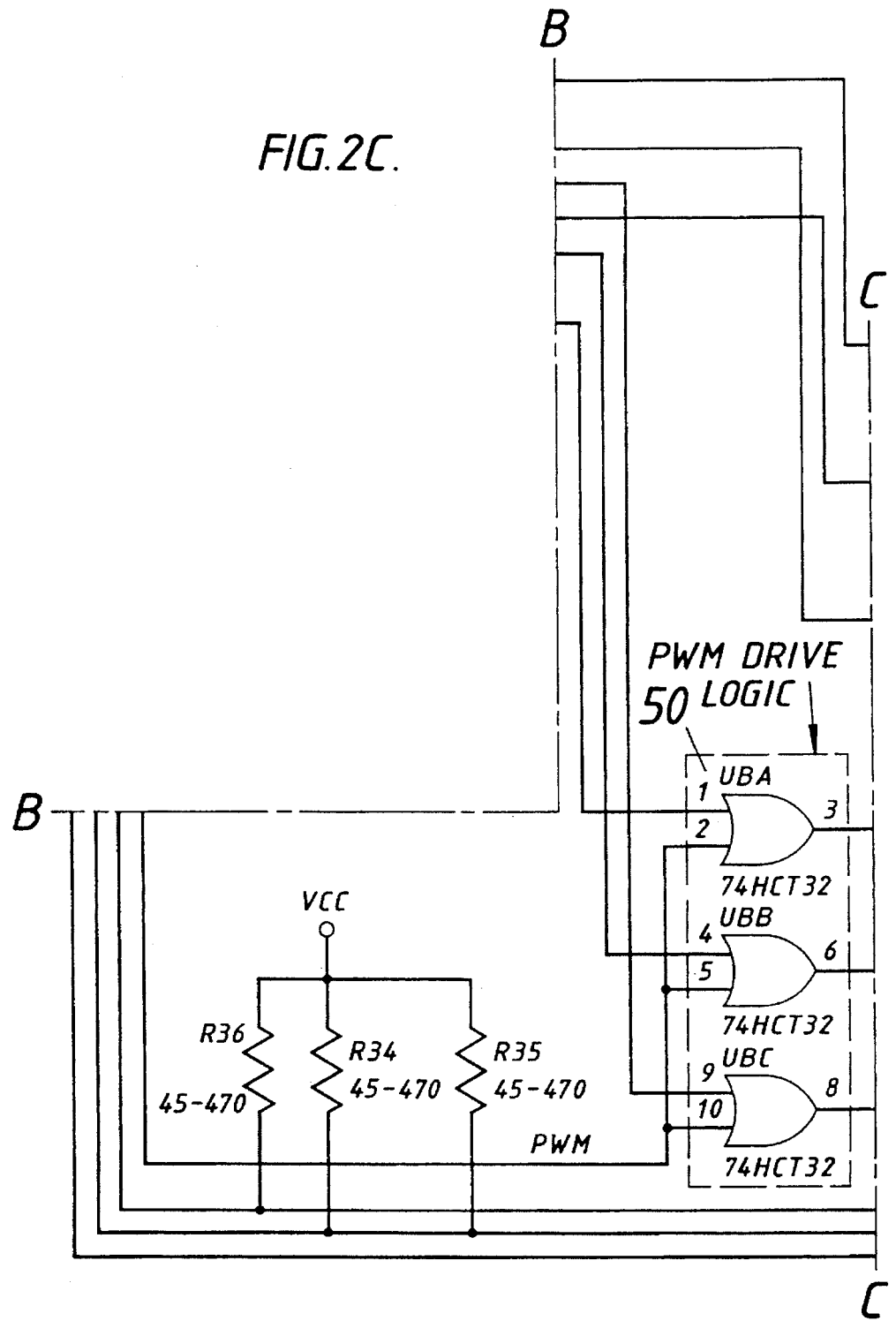
Figure 2E:
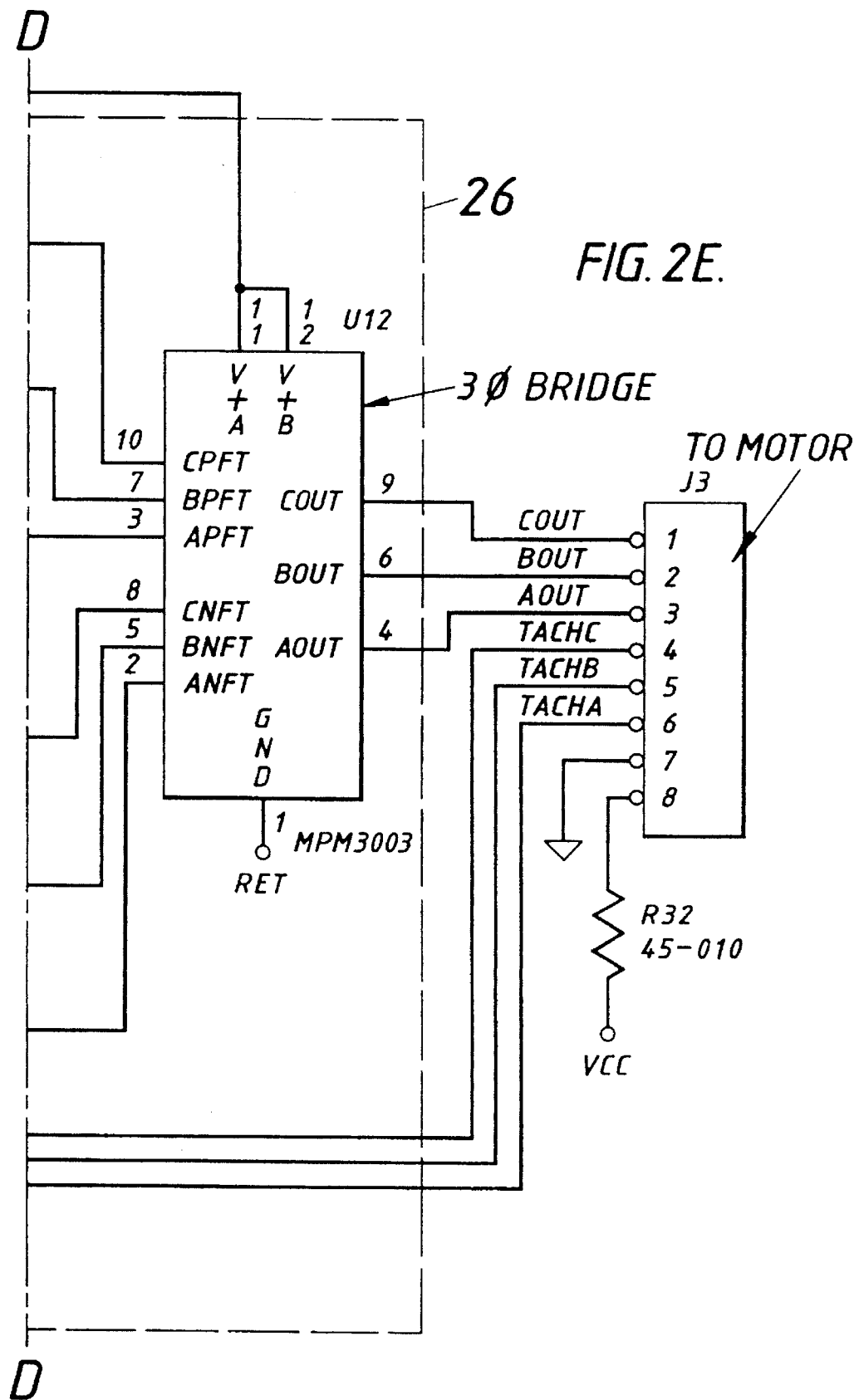

The present invention is illustrated in terms of a control system for controlling the speed of a brushless three-phase, DC motor. Referring now to the drawings, FIG. 1 is a general block diagram, and FIG. 2 is a more detailed electrical schematic, of the overall all-digital motor speed control system of this invention. Reference numeral 10 identifies a brushless, three-phase, DC motor having an armature 12. Preferably, the motor is obtained from BEI Kimco Magnetics Division of San Marcos, Calif., as its part No. DIH 23-20-BBNB. This motor has a plurality of conventional Hall-effect sensors 14 mounted about the armature to sense armature position.

The system includes a main digital signal processor (CPU) 16, preferably constituted as integrated circuit chip No. 87C51-PLCC. Main processor 16 is in direct digital communication with a drive controller 18, preferably also constituted as integrated circuit chip 87C51-PLCC. Processor 16 supplies a digital input speed signal RX indicative of a desired armature speed to the controller 18 over line 20. The controller 18, as will be described in detail below, supplies a digital output speed signal TX indicative of the actual armature speed to the processor 16 over line 22. Controller 18 also communicates with the processor 16 over a RESET line 24. Lines 20, 22, 24 are high speed buses capable of transmitting data at 375 kbaud. Preferably, communication lines 20, 22 and 24 are optical fibers. However, the main processor and the controller may communicate by means such as a parallel communication bus, a high speed serial hardwired interface or the like.

Upon receipt of the input speed signal RX, controller 18 executes a software program as set forth on pages A-1 through A-3 of the attached Appendix. Controller 18 generates a set of six commutation signals, two for each phase of the motor, together operative for rotating the armature. More specifically, the controller includes an interior look-up table having a listing of six commutation bit patterns, each pattern representing a discrete command for the armature at an angular position spaced 60 electrical degrees from the previous armature position. The commutation signals are fed through, and processed in, a three-phase bridge circuit 26, and optionally, through a bridge driver circuit (see FIG. 2), wherein three position control signals, one for each phase, are output to the motor 10. The Hall-effect sensors 14 sense rotation of the armature and generate two-state Hall-effect signals which advise the controller 18 when to generate the commutation signals.

Figure 3:
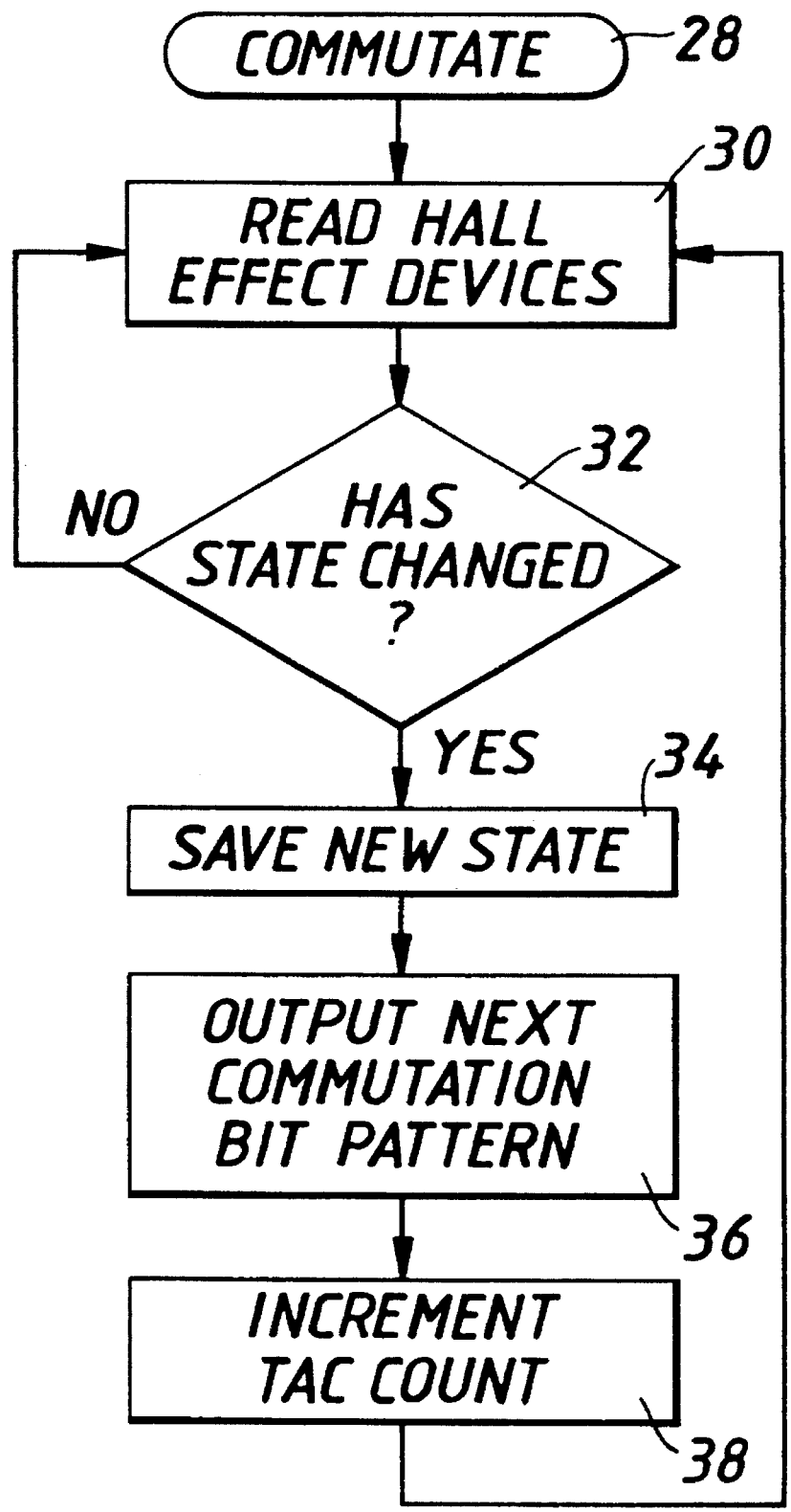
FIG. 3 is a flow chart depicting part of the operation of the controller.

This latter aspect of the controller 18 is displayed in the flow chart of FIG. 3. The generation of the commutation signals is indicated by block 28. The reading of the Hall-effect sensors is denoted by block 30. If the controller 18 recognizes that the state of the Hall-effect signals has changed (block 32), then the new state is saved (block 34) and the next commutation bit pattern is output to the motor (block 36). Thereafter, an internal counter operative for generating a tachometer (TAC) signal is incremented (block 38) prior to the next reading of the Hall-effect sensors. The tachometer signal is eventually processed to generate the aforementioned output speed signal TX. If the state of the Hall-effect sensors did not change in block 32, this indicates that the armature has not moved 60 electrical degrees and, hence the controller attempts to read the Hall-effect sensors again in block 30.

Controller 18 also generates in response to command data from the processor 16, a digital pulse width modulated (PWM) signal having a duty cycle established by said command data. The PWM signal is carried on a carrier signal having a frequency which, in the preferred case, is 3.90625 kHz. Controller 18 has an internal software PWM timer which, in the preferred case, establishes a PWM cycle of 256 microseconds. The PWM cycle has a high and a low state. The PWM output is allowed to continue running during the high state, but is re-set to OFF in the low state. The command data controls how long the PWM timer runs; in the preferred case, from 14–242 µs. In this way, the duty cycle of the PWM signal is controlled from 5.47%–94.53%.

Figure 4:
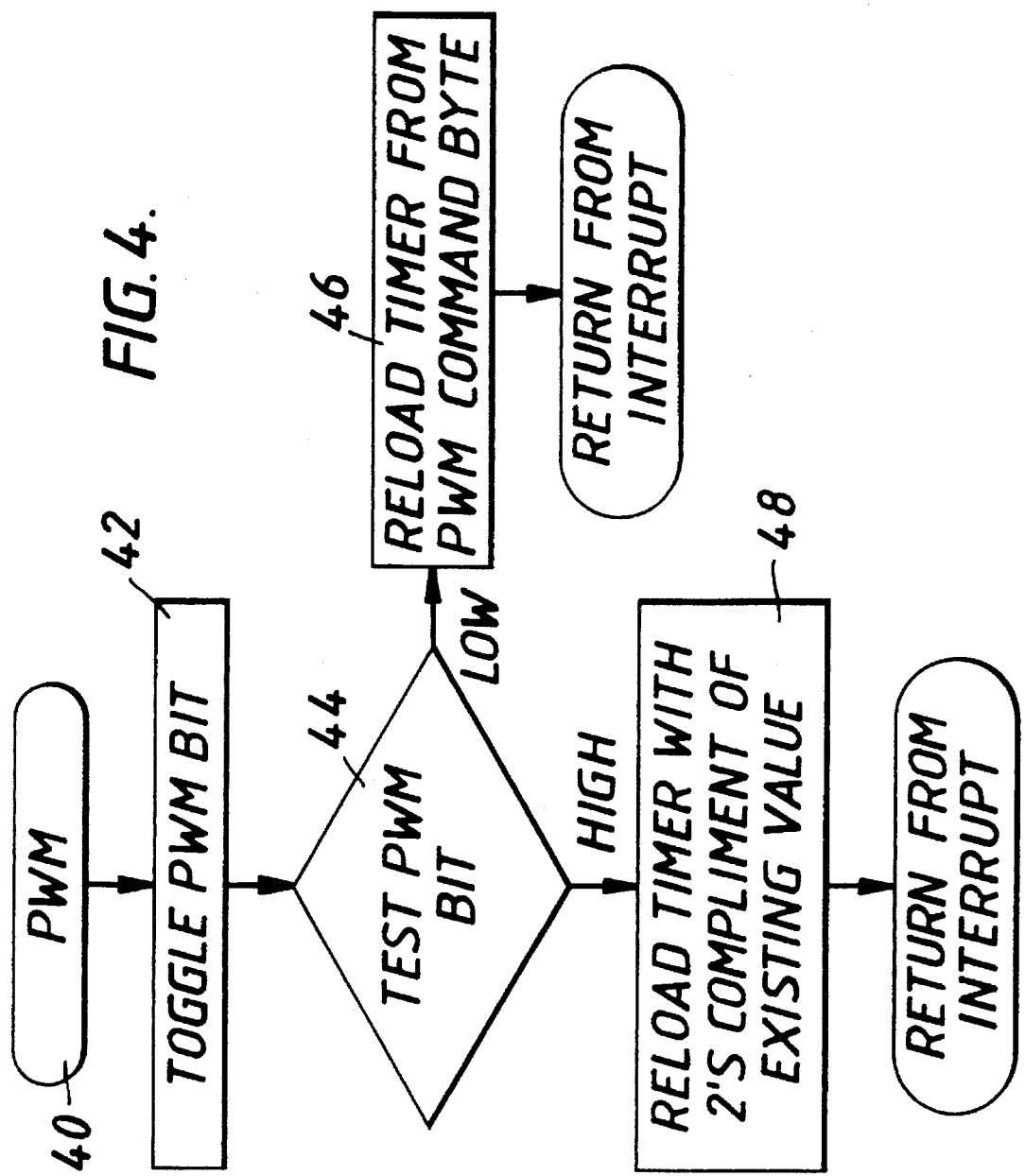
FIG. 4 is a flow chart depicting another aspect of the operation of the controller.

This aspect of the controller operation is depicted in FIG. 4. Block 40 represents the generation of the PWM signal. The controller toggles and generates a two-state PWM bit (block 42) and tests the state of the PWM bit in block 44. If the PWM bit has a low state, then, as depicted in block 46, the PWM timer is re-loaded from a command byte supplied by type processor 16. If the PWM bit has a high state, then the PWM timer is re-loaded with the 2's complement of its existing value (block 48).

As best shown in FIG. 1, the PWM signal is fed to a drive logic unit 50 which, as shown in FIG. 2, comprise three or gates to which three of the commutation signals are conveyed. Unit 50 generates switching signals for the bridge 26. In turn, the bridge 26 generates, for each phase, the aforementioned modulated control signal having an on-state and an off-state.

Figure 5:
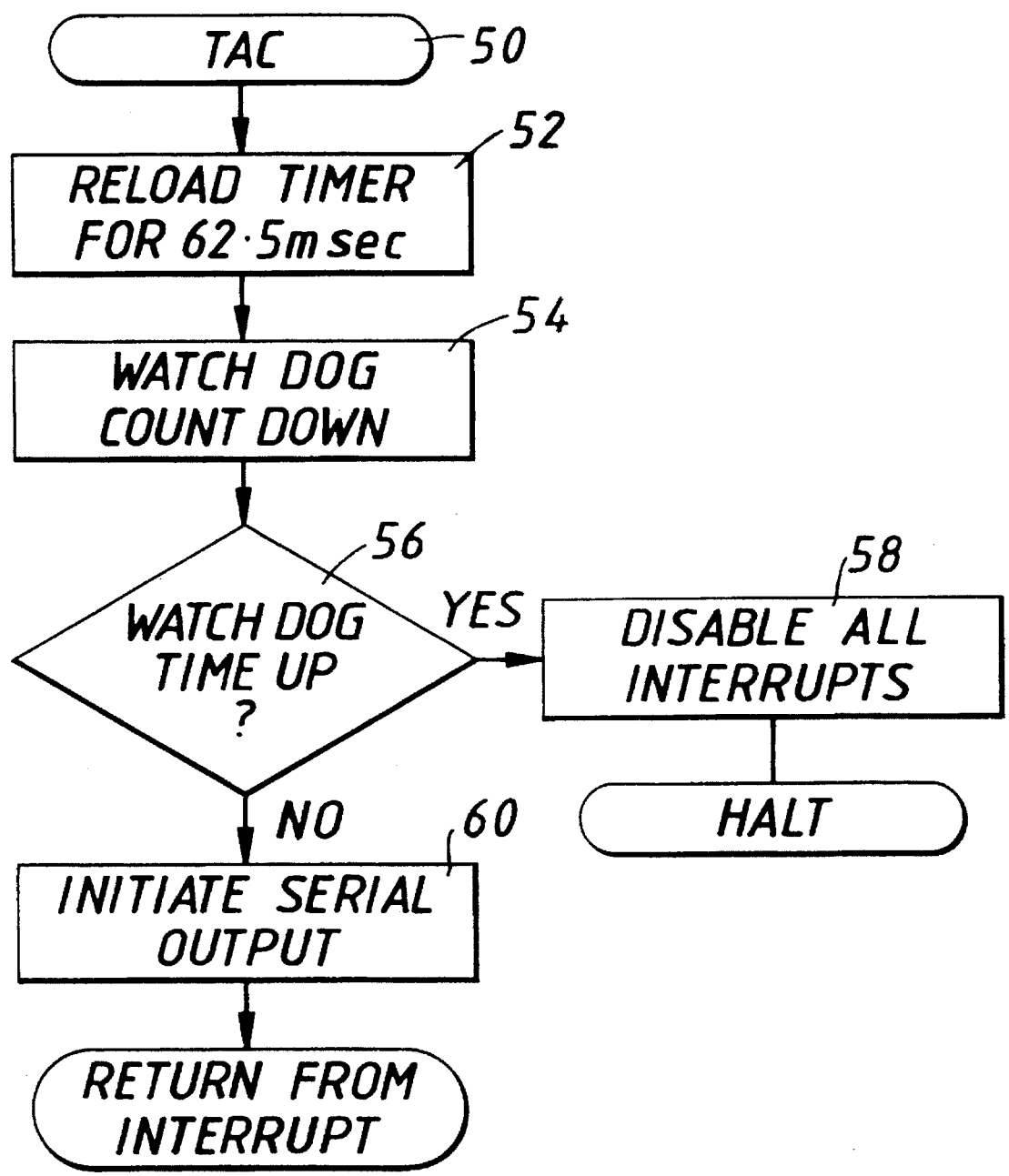
FIG. 5 is a flow chart depicting still another aspect of the operation of the controller.

As shown in the flow chart of FIG. 5, the Hall-effect sensors, as previously mentioned, send TAC signals back to the controller (block 50) and, more specifically, TAC signals are accumulated as they occur every 62.5 ms in a TAC timer (block 52). The resulting count from the TAC counter is processed into a tachometer signal which is processed by the controller and fed back to the processor 16 over line 22, and is indicative of the actual speed of the motor.

In accordance with another feature of this invention, a watchdog counter (block 54 in FIG. 5) has a pre-set count of, for example, 500 ms. Upon receipt of the TAC timer interrupt, the watchdog counter counts down. If, as determined in block 56, the 500 ms has elapsed, then the entire system is shut down (block 58). If, however, the watchdog time has not elapsed, then the command data from the processor 16 is sent to the controller over line 20 as denoted in block 60.

Figure 6:
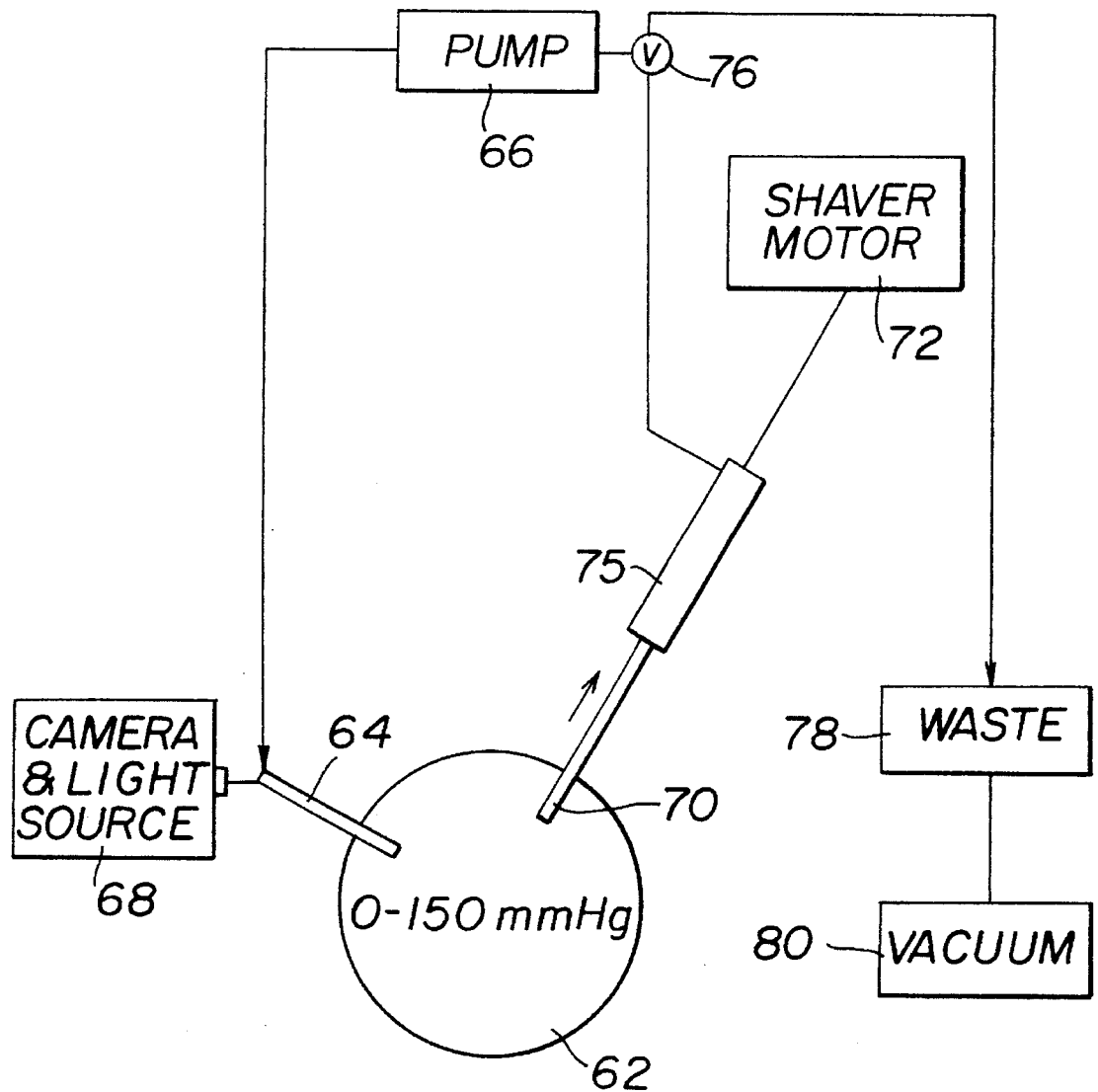
FIG. 6 is a schematic block diagram of a surgical procedure, using the system of the invention.

FIG. 6 is a schematic block diagram showing a setup of a typical modern surgical procedure, e.g. of an arthroscopy or laparoscopy. A joint or another area of the patient being operated on is shown at 62. A first curet 64 is introduced into the area and is attached to a source of saline solution, i.e. a pump 66 which maintains a positive pressure in the joint, e.g. at 0 to 150 mm Hg gauge. A video camera and light source 68 are also connected to the curet 64 for viewing the area and display on a T.V. monitor (not shown). A second canula 70 with a surgical instrument at its end is also introduced into the area 62. The instrument here is a shaver with a motor drive 74. The saline, blood and debris from the cutting are removed from the area through a hollow in the canula 70 and then through hose 74 which passes between a pinch valve 76 located on the pump housing 66 and which may help regulate flow from the area, and then to a waste collector 78 and to a vacuum 80 which typically maintain a pressure of 150 to 760 mm Hg absolute. Between the canula 70 and hose 74 is a tool 75 which supports the canula, the instrument therein and controls for the flow and application of vacuum.

It is important in such procedures that the pressure in the area 62 is constant. This is particularly difficult to maintain in the area of a joint where the mechanical dimensions of the joint are constantly changing, leaking and is an unstable, unsealed area. As the surgeon operates the surgical tool, opening and closing the connection to the vacuum and removing bits of tissue with bits of fluid flows, there is a constant variable, and quickly variable vacuum. It is essential for good surgical procedures that the pressure in the surgical area be constant. Particularly important is that the pressure never become too large, as this would injure the patient. Constant pressure is directly related to accurate control over the velocity of the saline flowing into the area 62. Small changes of pump speed yield very large changes in pressure. It has been found that with the control system of the present invention, a constant pressure can be provided within very tight tolerances. This is particularly achieved with a pulse driven motor in the pump, whose duty cycle can be varied, and whose frequency of revolution can also be varied from a fraction of an RPM to, for example, 5000 RPM. Typical flow rates into a surgical area are from 0.0 to 2.5 liters per minute.

Figure 7:
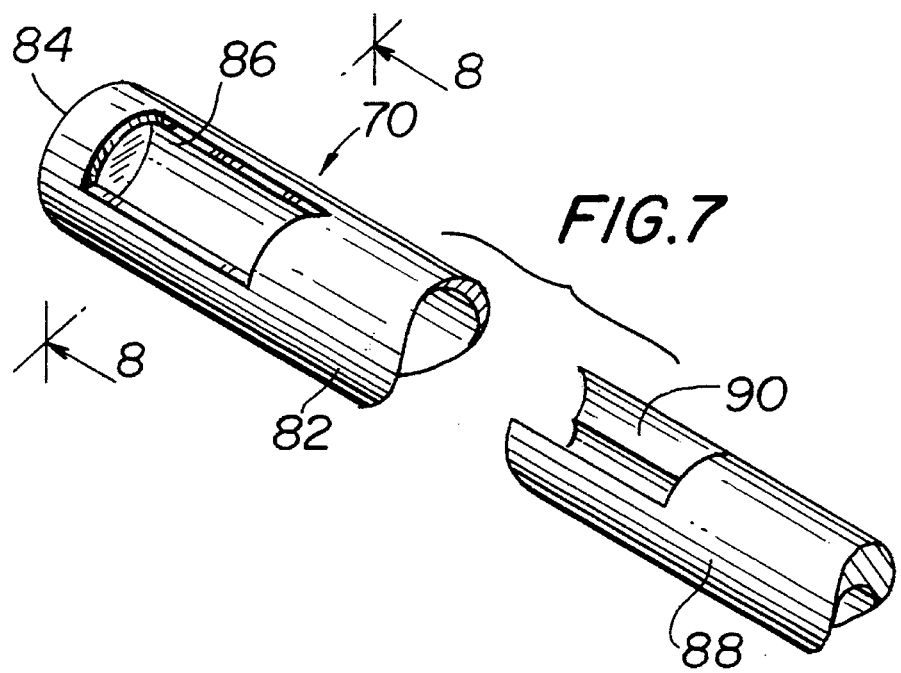
FIG. 7 is a perspective view of a surgical tool.

FIG. 7 is a schematic perspective, partially cut away, exploded view of part of a surgical router, which would appear at the end of the canula 70. A tube 82 closed at its distal end 84 has an opening which describes typically a cut-out section 86. The router 88 also a hollow tube, has a cutting surface with sharp edges at its distal end region 90. The router is motor driven and rotates inside the tube 82. The vacuum is drawing and fluids and debris are removed through the central hollow.

The router is typically driven at a constant speed, and rotates in one direction, driven by a motor within the shaver 72. It is desirable to control accurately the torque applied to the router, because if the torque is too large, e.g. due for example to a piece of bone or metal or other fragment getting caught in the spinning tube 88, the router itself or the tube 82, or the canula 70 may shatter with the result of spraying debris into the patient's joint. The debris, then, must be removed which is not an easy task. Also, there is an attendant trauma in the region. The control system of the present invention provides such a torque control. The system of the present invention applies a voltage or electrical drive energy, e.g., typically a series of pulses with a particular duty cycle. A digital tachometer measures the actual speed of the motor, and there is a table look-up which compares the speed with the output of the wave form for driving the router. When something gets stuck inside the curet or router the motor will normally need more power, and will thus will call for increased duty cycle in the form of more voltage or more current. The table look-up compares the duty cycle, or current, or voltage with the speed of the motor, and if the speed (it being noted that the motor and the curet are linked together), if the speed is too slow for the applied power, then the controller will drop the duty cycle, or will drop the voltage or current, and this will cut down on the torque, and thus will avoid possible fracture of the router or the tube 82. The surgeon may then observe through the camera 68 what is the condition at the end of the canula, e.g. if something is stuck, and increase the flow of saline or manipulate the tool to remove the clogging; and if need be, to change the tool.

Figure 8:
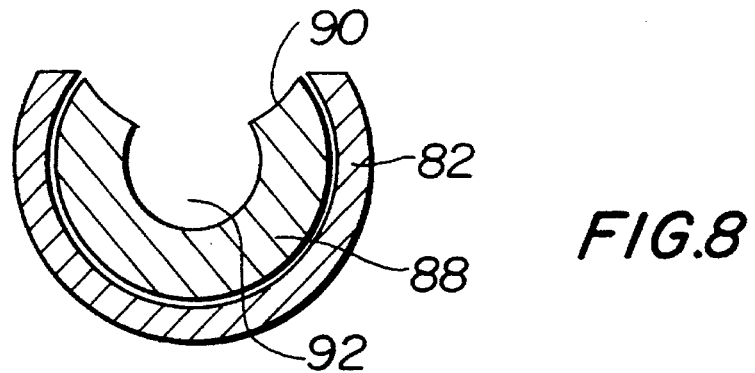
FIG. 8 is a cross-sectional view through FIG. 7.

FIG. 8 is a cross-sectional view through the canula of FIG. 7 but with the router inserted therein. The router 82 with its cutting edge 90 in the present invention may be driven to rotate one way, and then another, i.e. to oscillate, e.g. to rotate precisely 360° clockwise, and then 360° counter-clockwise, and repeat. Typical cycle time for a rotation is 0.5 seconds or 120 oscillations per minute. Surgeons have long sought such a tool, as it is believed that it would improve cutting. As the router body 88 rotates one way and then the other, tissue that moves into the opening 90 is cut, and is then removed by a vacuum, and flushing of a saline solution through the aperture 92, which feeds ultimately to the hose 74.

It is understood that the use of oscillatory motion is not limited to routers, but may be used for drills, circular rasps, rotating scalpels, and a full range of motor driven and controlled tools.

Figure 9:
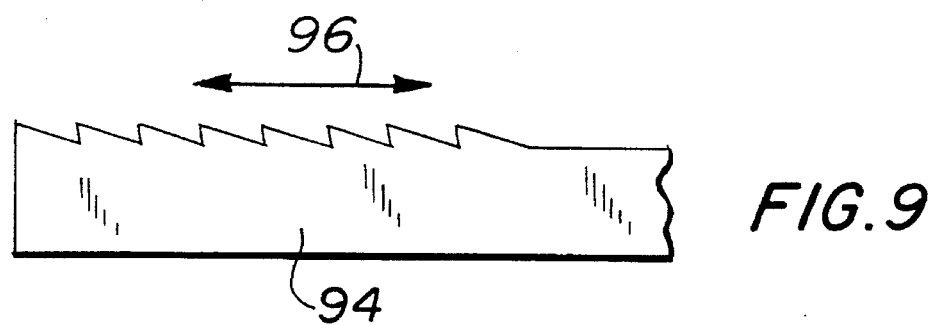
FIG. 9 is a schematic side view of a rasp.

FIG. 9 is a schematic side view of a surgical reciprocating rasp. The rasp 94 moves back and forth in a linear direction as shown by the arrows 96. It is connected at one end to a motor drive, which is a reciprocating motor or solenoid. The reciprocating motor would have a single Hall-effect sensor, which gives an indication of position. The control of the reciprocating rasp in the invention is done completely by the electrical system, and there are no springs connected to the rasp, and no mechanical resonance devices connected to the rasp. All of the force to move it to and fro is from the electrical control signal. The precise control for the reciprocating motion is achieved by having the control of the invention, provide a series of step control pulses, which force the linear solenoid motor output backward and forward. Each cycle may have a series of smaller pulses of uniform or different widths, as experimentation will indicate, to move the rasp firmly and accurately backward and forward. The tachometer feed back is then fed and a table look-up and the control can adjust for additional force to be applied, depending upon what is being cut or shaved by the tool. The wider the pulse, and the closer the pulses in each cycle are to each other, the more force that is applied. It is expected that to provide a smooth operation and to avoid possible vibration of the canula, the pulses close to the end and at the beginning of each cycle may be narrower than the pulses at the center of each cycle. In other words, the force of cutting can be controlled by the duty cycle, which would be adjustable throughout the surgical procedure, and as called for by measurement of the tachometer, and the output of the pulses. Again, it is emphasized that the control of the rasp is purely electrical without springs, without mechanical resonances, or other mechanical means.

A typical motion of a reciprocating rasp is about ¼ of an inch or about 250 thousandths, and with a cycle time of 1 second.

In another embodiment of the invention, the system provides two signals to the motor or solenoid. One, being a low frequency signal, e.g. with cycle time of one second, and the other being a high frequency signal of, e.g., with a cycle time of one millisecond. The low frequency signal is described as above, and the high frequency signal is substantially similar but more rapid. The compound signals give a compound motion to the reciprocating rasp, i.e. a dithering motion at high frequency with a short length, for example, in the range of 20 to 40 thousandths superimposed upon the slower stroke of approximately 250 thousandths. For certain surgical applications, this should prove advantageous. The control for both the high frequency and low frequency signal and the drive for them, would be a system as set forth herein.

It should be appreciated that the present invention is a control system for an electrical output, which drives for example, an electrical stepper or brushless motor with a rotating or reciprocating output. It provides precise control of both the force or torque, which the motor will produce, and also the velocity or speed at which the motor rotates or reciprocates. This is achieved due to the nature of the electrical output signal, and the table look-up in the controller, which table look-up can be adjusted easily and electronically, e.g. from a computer terminal for the various applications which the motor will be used, and the loads and degree of accuracy placed upon those motors.

It will be understood that each of the elements described above, or two or more together, also may find a useful application in other types of constructions differing from the types described above.

While the invention has been illustrated and described as embodied in an all-digital speed control system for brushless three-phase DC motor, it is not intended to be limited to the details shown, since various modifications and structural changes may be made without departing in any way from the spirit of the present invention.

What is claimed is:

1. An all-digital control system for a motor having an armature, comprising:

(a) a main digital signal processor for supplying a digital input command signal indicative of a desired motor operation;

(b) a drive controller in digital communication with the main processor, for generating, for each phase of the motor, and in response to the command signal, a digital commutation signal to move the armature, and a digital pulse width modulated signal having a duty cycle established by the input command signal;

(c) switching means in digital communication with the controller, for generating, for each phase, and in response to each commutation signal and each pulse width modulated signal, a digital two-state control signal having an on-state which lasts for said duty cycle;

(d) means in digital communication with the controller, for generating, for each phase, a digital tachometer signal indicative of armature position;

(e) said controller being further operative for processing the tachometer signal, to generate a digital output signal indicative of the actual armature speed or position, and for communicating the digital output signal to the main processor, said controller including a look-up table having bit patterns, each corresponding to a different armature position.

2. The system according to claim 1, wherein the main processor and the drive controller are interconnected by, and digitally communicate through, a parallel bus or serial optical fibers.

3. The system according to claim 2, wherein said pulse width modulated signal for a second phase is superimposed on said pulse width modulated signal for a first phase to provide a compound motion of said motor.

4. The system according to claim 3 further comprising a connector adapted to connect a surgical instrument to said system so that said compound motion is provided by a motor in the surgical instrument.

5. The system according to claim 4 where said motor is a linear motor having fore and aft motion.

6. The system according to claim 5 wherein said instrument is a reciprocating rasp with a first signal driving said rasp with a stroke length of about 250 thousandths of an inch, and a second signal driving said rasp with a stroke length of about 20 to 40 thousandths of an inch.

7. The system according to claim 5 wherein the force in each motion of said instrument is exclusively controlled by the duty cycle of each of said first-phase and second-phase pulse width modulated signals.

8. The system according to claim 1, further comprising a second look-up table for modulating said pulse width modulated signal.

9. The system according to claim 1, wherein the pulse width modulated signal has two states, and wherein the controller includes timer means having a timer output signal whose duration is established by the state of the pulse width modulated signal.

10. The system according to claim 1, wherein the controller includes watchdog timer means having a predetermined watchdog time, and wherein the controller includes shutdown means for ceasing generation of the commutation signals upon elapse of said watchdog time without receipt of the input command signal.

11. The system according to claim 1, wherein the command signal provides oscillatory motion of a rotary motor, said motor further comprising an output for connection to a surgical instrument so that the system inputs said oscillatory motion to said instrument.

12. The system according to claim 11, wherein said surgical instrument is an oscillatory shaver.

13. The system according to claim 12, wherein said shaver oscillates 360° in each direction at a rate of approximately 120 rpm.

14. The system according to claim 1, wherein said motor is a rotary motor and comprises an output for connection to a surgical instrument, and said system further comprising a control for limiting torque applied to said output so that said torque limiting control regulates the duty cycle of said pulse width modulated signal and excessive torque is not applied to said instrument.

15. The system according to claim 14, wherein said torque limiting control compares motor speed as indicated by said digital tachometer signal with the corresponding duty cycle of the control signal which is proportional to motor torque.

16. An all-digital speed control system for a motor having an armature, comprising:

(a) a main digital signal processor for supplying a digital input speed signal indicative of a desired armature speed;

(b) a drive controller in direct digital communication with the main processor, for generating, for each phase of the motor, and in response to the input speed signal, a digital commutation signal to move the armature, and a digital pulse width modulated signal having a duty cycle established by the input speed signal;

(c) switching means in digital communication with the controller, for generating, for each phase, and in response to each commutation signal and each pulse width modulated signal, a digital two-state speed control signal having an on-state which lasts for said duty cycle;

(d) means in direct digital communication with the controller, for generating, for each phase, a digital tachometer signal indicative of armature position;

(e) said controller being further operative for processing the tachometer signal, to generate a digital output speed signal indicative of the actual armature speed, and for directly digitally communicating the output speed signal to the main processor, said controller including a look-up table having commutation bit patterns, each corresponding to a different armature position.

17. The system according to claim 16, wherein the duty cycle of the pulse width modulated signal lies in an approximate range between 5% and 95%.

18. The system according to claim 16, wherein the pulse width modulated signal is carried on a signal carrier having a frequency of approximately 3.9 kHz.

19. The system according to claim 16, wherein the pulse width modulated signal has two states, and wherein the controller includes timer means having a timer output signal whose duration is established by the state of the pulse width modulated signal.

20. The system according to claim 16, wherein the controller includes watchdog timer means having a predetermined watchdog time, and wherein the controller includes shutdown means for ceasing generation of the commutation signals upon elapse of said watchdog time without receipt of the input speed signal.

21. An all-digital control system for a motor having an armature, comprising:

(a) a main digital signal processor for supplying a digital input command signal indicative of a desired armature speed;

(b) a drive controller in digital communication with the main processor, for generating, for each phase of the motor, and in response to the command signal, a digital commutation signal to move the armature, and a digital pulse width modulated signal having a duty cycle established by the input command signal;

(c) switching means in digital communication with the controller, for generating, for each phase, and in response to each commutation signal and each pulse width modulated signal, a digital two-state control signal having an on-state which lasts for said duty cycle;

(d) means in digital communication with the controller, for generating, for each phase, a digital tachometer signal indicative of armature position;

(e) said controller being further operative for processing the tachometer signal, to generate digital output signal indicative of the actual armature speed, and for communicating the digital output signal to the main processor; and (f) a look-up table in the main processor adapted to provide a signal to said drive controller in response to said digital output signal indicative of the actual armature speed, that indicates a voltage or electrical drive energy needed to produce said desired armature speed.

22. The system according to claim 21 wherein signals between said processor and said controller are optical.

23. The system of claim 21, wherein said controller directly digitally communicates the output speed signal to the main processor.

24. The system of claim 23, wherein signals between said processor and said controller are optical.

* * * * *

UNITED STATES PATENT AND TRADEMARK OFFICE
CERTIFICATE OF CORRECTION

Page 1 of 4

PATENT NO. : 5,563,481

DATED : October 8, 1996

INVENTOR(S) : Kenneth W. Krause

It is certified that error appears in the above-identified patent and that said Letters Patent is hereby corrected as shown below:

Col. 7, before the claims insert --Appendix A-- (attached).

Signed and Sealed this

Thirtieth Day of June, 1998

*Attest:*

BRUCE LEHMAN

*Attesting Officer*     *Commissioner of Patents and Trademarks*

APPENDIX

```
1   ;--------------------------------------------------------------------
2   ; PWMV21 Serial Brushless Motor Driver for the 8051
3   ; KWK 10/12/91
4   ;
5   ; REV 1 01/23/92 KWK   Add watchdog time out with shut down
6   ;--------------------------------------------------------------------
7   ;                       SPECIFICATIONS
8   ;BRUSHLESS MOTOR
9   ;   Phases / winding type:    3ø / Y
10  ;       Number of poles:      8
11  ;       Sensor sequence:      3 sensors @ 120° electrical
12  ;
13  ;PWM OUTPUT
14  ;       Carrier frequency:    3.90625 kHz
15  ;           Minimum PWM:      5.5 %
16  ;           Maximum PWM:      94.5 %
17  ;         PWM resolution:     1 usec (.390625 %)
18  ;             PWM jitter:     2 usec max
19  ; Commutation phase error:    4 electrical degrees max
20  ;
21  ;TACHOMETER OUTPUT
22  ;               Format:       Integral RPM / 40
23  ;               Range:        0 - 10,200 rpm
24  ;           Resolution:       40 rpm
25  ;                 Rate:       62.5 msec
26  ;
27  ;SERIAL I/O LINK
28  ;   Communication protocol:   Mode 2, multiprocessor communication,
29  ;                             asynchronous, bi-directional 3 byte
30  ;                             packet
31  ;             Baud rate:      375 kbaud
32  ;         Packet format:      sync_byte, data_byte, data_byte
33  ;                 Input:      PWM command byte (14 - 242)
34  ;                Output:      Tachometer byte (0 - 255)
35  ;              Watchdog:      .5 second command refresh window else
36  ;                             shutdown. Hardware reset required.
37  ;--------------------------------------------------------------------
38  ;8051 REGISTER USEAGE
39  ;               r7:   Hall pattern input buffer
40  ;               r6:   Tac count
41  ;               r5:   PWM command
42  ;               r4:   Receive character counter
43  ;               r3:   Transmit character counter
44  ;               r2:   Receive character buffer
45  ;               r1:   Watchdog counter
46  ;--------------------------------------------------------------------
47  ; PROGRAM AREA
48  ;
49         defseg  PWM,absolute
50         seg     PWM
51         jb      p1.7,start     ; Brushless motor driver
52         ajmp    stepper        ; Stepper motor driver
53  ;
```

A-1

APPENDIX

```
                                54   ; PWM output to p1.3 on timer 0 interrupt
                                55   ;
            =0008               56          org     08h             ; Timer 0 interrupt location
0008 B2 93                      57          cpl     p1.3            ; Toggle pwm out
000B 20 93 03'                  58          jb      p1.3,negate
0010 8D 8C                      59          mov     th0,r5          ; Reload pwm when p1.3 = 0
0012 32                         60          reti
0013 63 8C' FF                  61   negate xrl     th0,#0FFh
0016 05 8C                      62          inc     th0             ; 2's compliment
0018 32                         63          reti
                                64   ;
                                65   ; Timer 1 interrupt location
                                66   ;
            =0018               67          org     18h
001B 20 97 30'                  68          jb      p1.7,tac_out    ; Brushless routine
001E 2128                       69          ajmp    step_timer      ; Stepper routine
                                70   ;
                                71   ; Serial port interrupt location
                                72   ;
            =0023               73          org     23h
0023 20 97 02'                  74          jb      p1.7,pwm_cmd    ; Brushless SIO routine
0026 2128                       75          ajmp    step_com        ; Stepper serial routine
                                76   ;
                                77   ; Receive PWM command
                                78   ;
0028 10 99 23'                  79   pwm_cmd jbc    ti,talk         ; Go to transmit interrupt routine
002B C2 98                      80          clr     ri              ; Clear interrupt indicator
002D 30 9D 04'                  81          jnb     sm2,receive     ; Data byte receive
0030 AA 99                      82          mov     r2,sbuf         ; Get character from receive buffer
0032 BA FF 04'                  83          cjne    r2,#0FFh,nosync ; Return if not sync byte
0035 7C 02                      84          mov     r4,#2           ; Set incoming character counter
0037 C2 9D                      85          clr     sm2             ; Prepare to receive data bytes
0039 32                         86   nosync reti
003A DC 0F'                     87   receive djnz   r4,char1        ; Go to first character processor
003C C0 E0                      88          push    acc             ; Second character processor
003E E5 99                      89          mov     a,sbuf          ; Get second character
0040 B5 02 03'                  90          cjne    a,2,err         ; Error if different from first character
0043 FD                         91          mov     r5,a            ; Make command data available to PWM routine
0044 79 08                      92          mov     r1,#8           ; Reset watchdog counter
0046 D0 E0                      93   err    pop     acc
0048 D2 9D                      94          setb    sm2             ; Restore communication mode
004A 32                         95          reti
004B AA 99                      96   char1  mov     r2,sbuf         ; Snatch first character
004D 32                         97          reti
                                98   ;
                                99   ; Tachometer data out on transmit interrupt
                                100  ;
004E D8 03'                     101  talk   djnz    r3,notdone      ; Send 2 tac data bytes
0050 7E 00                      102         mov     r6,#0           ; Reset tac
0052 32                         103         reti
0053 8E 99                      104  notdone mov    sbuf,r6         ; Output tac data byte
0055 32                         105         reti
                                106  ;
```

A-2

APPENDIX

```
                              107  ; Initiate tachometer output to serial port on timer 1 interrupt
                              108  ;
0056 75 88' E1                109  tac_out  mov    t11,#0E1h       ; Set for 62.5 msec (5usec access)
0059 75 8D' 08                110           mov    th1,#08h
005C 09 06'                   111           djnz   r1,cont         ; Watchdog count down
005E C2 AF                    112           clr    ea              ; Turn off all interrupts
0060 D2 93                    113           setb   p1.3            ; Turn off n channel fets
0062 80 FE'                   114           sjmp   $               ; Lock up
0064 75 99' FF                115  cont     mov    sbuf,#0FFh      ; Send sync to initiate tac output
0067 78 03                    116           mov    r3,#3           ; Set transmit character counter
0069 32                       117  tac_end  reti
                              118  ;
                              119  ; Initialize 8051
                              120  ;
006A 20 96B 05'               121  start    jb     p1.6,st1        ; ccw = p1.6 hi
006D 90 00AE'                 122           mov    dptr,#ccw-1     ; ccw = p1.6 lo
0070 80 03'                   123           sjmp   st2
0072 90 00A8'                 124  st1      mov    dptr,#cw-1      ; Commutation translation table base address
0075 7F 00                    125  st2      mov    r7,#0           ; Force pass through main loop to start
0077 7E 00                    126           mov    r6,#0           ; Reset tac count
0079 70 0E                    127           mov    r5,#0Eh         ; Minimum PWM
007B 79 08                    128           mov    r1,#8           ; Initialize watchdog
007D 75 89' 12                129           mov    tmod,#12h       ; Set timer 0 for mode 2 & timer 1 for mode 1
0080 8D 8A                    130           mov    t10,r5          ; Set timer 0 for minimum PWM
0082 75 8C' F2                131           mov    th0,#0F2h
0085 D2 B9                    132           setb   pt0             ; Set timer 0 priority
0087 75 8B' E1                133           mov    t11,#0E1h       ; Set timer 1 for 62.5 msec (5usec access)
008A 75 8D' 08                134           mov    th1,#08h
008D 43 87' 80                135           orl    pcon,#80h       ; Double baud rate
0090 75 98' 88                136           mov    scon,#088h      ; Serial mode 2, 375 kbaud, multiprocessor
0093 75 A8' 9A                137           mov    ie,#9Ah         ; Enable appropriate interrupts
0096 75 88' 50                138           mov    tcon,#50h       ; Turn timers on
                              139  ;
                              140  ; Main control loop
                              141  ;
0099 E5 90                    142  main     mov    a,p1            ; Main commutation / tachometer loop
009B 54 07                    143           anl    a,#7
009D B5 07 02'                144           cjne   a,7,comm        ; Check for change from previous
00A0 80 F7'                   145           sjmp   main
00A2 FF                       146  comm     mov    r7,a            ; Save previous state
00A3 93                       147           movc   a,@a+dptr
00A4 F5 A0                    148           mov    p2,a            ; Commutate
00A6 0E                       149           inc    r6              ; Increment tac count
00A7 80 F0'                   150           sjmp   main
                              151  ;
                              152  ; Motor phase excitation table
                              153  ;
00A9 23 0E 08 38 32           154  cw       db     23h,0Eh,08h,38h,32h,2Ch ; Commutation bit array
00AE 2C
00AF 2C 32 38 08 0E           155  ccw      db     2Ch,32h,38h,08h,0Eh,23h ; Commutation bit array
00B4 23
```

A-3